(12) United States Patent
Foster et al.

(10) Patent No.: US 8,676,350 B2
(45) Date of Patent: Mar. 18, 2014

(54) ACTIVE FIXATION IMPLANTABLE LEAD WITH ROTATION STOP FEATURES

(75) Inventors: Daniel J. Foster, Lino Lakes, MN (US); Toua Vang, St. Paul, MN (US); Kimberly A. Jorgensen, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 150 days.

(21) Appl. No.: 13/289,664

(22) Filed: Nov. 4, 2011

(65) Prior Publication Data

US 2012/0158108 A1 Jun. 21, 2012

Related U.S. Application Data

(60) Provisional application No. 61/423,376, filed on Dec. 15, 2010.

(51) Int. Cl.
*A61N 1/00* (2006.01)

(52) U.S. Cl.
USPC .......................................... 607/119; 607/127

(58) Field of Classification Search
USPC .......... 607/115–116, 119–120, 122, 126–127
See application file for complete search history.

(56) References Cited

U.S. PATENT DOCUMENTS

| | | | | |
|---|---|---|---|---|
| 4,886,074 | A * | 12/1989 | Bisping | 607/116 |
| 7,029,466 | B2 * | 4/2006 | Altman | 604/508 |
| 2003/0083727 | A1 | 5/2003 | Casavant et al. | |
| 2009/0192578 | A1 * | 7/2009 | Biggs | 607/116 |
| 2010/0211149 | A1 | 8/2010 | Morgan et al. | |
| 2010/0222860 | A1 * | 9/2010 | Casella et al. | 607/127 |
| 2010/0305672 | A1 | 12/2010 | Felling et al. | |

FOREIGN PATENT DOCUMENTS

WO WO9810827 A1 3/1998

OTHER PUBLICATIONS

International Search Report and Written Opinion issued in PCT/US2011/059329, dated Mar. 28, 2012, 14 pages.

* cited by examiner

*Primary Examiner* — Christopher D Koharski
*Assistant Examiner* — Catherine Voorhees
(74) *Attorney, Agent, or Firm* — Faegre Baker Daniels LLP (57) ABSTRACT

An implantable medical electrical lead includes an extendable/retractable active fixation distal tip assembly. The distal tip assembly includes a shell having an internal cavity and a helix guide member extending at least partially across the cavity and including an axial surface. The distal tip assembly also includes a rotatable coupler within the cavity and a fixation helix fixedly attached to the coupler. The fixation helix engages the helix guide member such that rotation of the coupler and the fixation helix causes the coupler and the fixation helix to advance distally relative to the shell. The coupler further includes a distal rotation stop member protruding axially from the coupler configured to abut the axial surface of the helix guide member to delimit rotation and extension of the coupler and the fixation helix.

15 Claims, 6 Drawing Sheets

ACTIVE FIXATION IMPLANTABLE LEAD WITH ROTATION STOP FEATURES

CROSS-REFERENCE TO RELATED APPLICATION

This application claims priority to U.S. Provisional Application 61/423,376, filed Dec. 15, 2010, which is herein incorporated by reference in its entirety.

TECHNICAL FIELD

The present invention relates to implantable medical devices and relates more particularly to leads for cardiac rhythm management (CRM) systems.

BACKGROUND

Various types of medical electrical leads for use in cardiac rhythm management (CRM) and neurostimulation systems are known. For CRM systems, such leads are typically extended intravascularly to an implantation location within or on a patient's heart, and thereafter coupled to a pulse generator or other implantable device for sensing cardiac electrical activity, delivering therapeutic stimuli, and the like. The leads frequently include features to facilitate securing the lead to heart tissue to maintain the lead at its desired implantation site. Exemplary leads can include a helical fixation member that can be extended from the distal end of the lead and screwed into the cardiac tissue to fixate the lead in place.

SUMMARY

In Example 1, the present invention is an implantable medical electrical lead comprising a flexible insulative body, a connector, a first conductor, a first electrode, and a distal tip assembly. The flexible insulative body has a proximal end and an opposite distal end, and defines a longitudinal axis of the lead. The connector is coupled to the proximal end of the lead body and is configured for operatively coupling the lead to an implantable pulse generator. The first conductor extends within the lead body from the connector toward the distal end of the lead body, and the first electrode is coupled to the body and to the first conductor. The distal tip assembly is coupled to the distal end of the lead body and includes a shell, a coupler and a fixation helix. The shell has an outer wall defining a shell proximal end, an opposite shell distal end, and an internal cavity between the shell proximal and distal ends. The shell further includes a helix guide member extending at least partially across the cavity at or near the shell distal end and defining an axial surface and a distal opening. The coupler is rotatably disposed within the cavity and includes a proximal shaft portion and a distal shaft portion having a distal end, and further includes a distal rotation stop member protruding axially from the distal end of the distal shaft portion. The fixation helix is fixedly coupled to the distal shaft portion of the coupler and includes a distal portion extending at least partially through the distal opening of the shell. The fixation helix and the helix guide member are configured so that the fixation helix slidably contacts a portion of the helix guide member such that rotation of the coupler and the fixation helix causes axial translation of the coupler and the fixation helix relative to the shell between fully retracted and fully extended positions. The distal rotation stop member is configured to abut the axial surface of the helix guide member in the fully extended position so as to delimit further rotation and axial extension of the coupler and the fixation helix.

In Example 2, the implantable medical electrical lead of Example 1, further comprising a second conductor extending within the lead body and connected to the proximal shaft portion of the coupler, wherein the coupler and the fixation helix are electrically conductive and the fixation helix is operable as a second electrode.

In Example 3, the implantable medical electrical lead of either of Examples 1 or 2, wherein the cavity has a generally circular cross-sectional shape and the helix guide member has a generally semi-circular cross-sectional shape when viewed along the longitudinal axis of the lead, such that the distal opening has a generally semi-circular shape.

In Example 4, the medical electrical lead of Example 3, wherein the axial surface of the helix guide member includes a radiused region near an intersection of the axial surface of the helix guide member and an inner surface of the shell outer wall.

In Example 5, the medical electrical lead of any of Examples 1-4, wherein the distal end of the distal shaft portion of the coupler includes a distal radial face, and wherein the distal rotation stop member is disposed radially inward of the fixation helix and protrudes axially from the distal radial face.

In Example 6, the medical electrical lead of any of Examples 1-5, wherein the helix guide member extends radially inward of the outer wall of the shell.

In Example 7, the medical electrical lead of Example 6, wherein the helix guide member does not extend radially inward to the longitudinal axis.

In Example 8, the medical electrical lead of any of Examples 1-7, wherein the distal rotation stop member includes a pair of converging axial surfaces, and wherein one of the converging axial surfaces is configured to abut the axial surface of the helix guide member to delimit further rotation and extension of the coupler and the fixation helix.

In Example 9, the present invention is an implantable medical electrical lead comprising a flexible insulative body, a connector, a first conductor, and a distal tip assembly. The flexible insulative body has a proximal end and an opposite distal end, and defines a longitudinal axis of the lead. The connector is coupled to the proximal end of the lead body and is configured for operatively coupling the lead to an implantable pulse generator. The connector includes a rotatable terminal pin. The first conductor extends within the lead body from the connector toward the distal end of the lead body, and is fixedly coupled to the terminal pin and rotatable within the lead body. The distal tip assembly is coupled to the distal end of the lead body and includes a shell, a coupler, and a fixation helix. The shell has an outer wall defining a shell proximal end, an opposite shell distal end, and an internal cavity between the shell proximal and distal ends. The shell further includes a helix guide member extending across the cavity at or near the shell distal end and defining an axial surface and a distal opening. The coupler is rotatably disposed within the cavity and includes a proximal shaft portion connected to the first conductor such that rotation of the terminal pin causes rotation of the coupler, and a distal shaft portion having a distal end. The coupler further includes a distal rotation stop member protruding axially from the distal end of the distal shaft portion. The fixation helix fixedly is coupled to the distal shaft portion of the coupler and includes a distal portion extending at least partially through the distal opening of the shell. The fixation helix and the helix guide member are configured so that the fixation helix slidably contacts a portion of the helix guide member such that rotation of coupler and the fixation helix causes axial translation of the coupler and the fixation helix relative to the shell between fully retracted and fully extended positions. The distal rotation stop member is configured to abut the axial surface of the helix guide member in the fully extended position so as to delimit further rotation and axial extension of the coupler and the fixation helix.

In Example 10, the implantable medical electrical lead of Example 9, wherein the cavity has a generally circular cross-sectional shape and the helix guide member has a generally semi-circular cross-sectional shape when viewed along the longitudinal axis of the lead, such that the distal opening has a generally semi-circular shape.

In Example 11, the medical electrical lead of either of Examples 9 or 10, wherein the axial surface of the helix guide member includes a radiused region near an intersection of the axial surface of the helix guide member and an inner surface of the shell outer wall.

In Example 12, the medical electrical lead of any of Examples 9-11, wherein the distal end of the distal shaft portion of the coupler includes a distal radial face, and wherein the distal rotation stop member is disposed radially inward of the fixation helix and protrudes axially from the distal radial face.

In Example 13, the medical electrical lead of any of Examples 9-12, wherein the helix guide member extends radially inward of the outer wall of the shell.

In Example 14, the medical electrical lead of Example 13, wherein the helix guide member does not extend radially inward to the longitudinal axis.

In Example 15, the medical electrical lead of any of Examples 9-14, wherein the distal rotation stop member includes a pair of converging axial surfaces, and wherein one of the converging axial surfaces is configured to abut the axial surface of the helix guide member to delimit further rotation and extension of the coupler and the fixation helix.

In Example 16, the present invention is an implantable medical electrical lead comprising a flexible insulative body, a connector, a torque transmission member, and a distal tip assembly. The flexible insulative body has a proximal end and an opposite distal end, and defines a longitudinal axis of the lead. The connector is coupled to the proximal end of the lead body and is configured for operatively coupling the lead to an implantable pulse generator. The torque transmission member extends within the lead body and is accessible from the connector. The distal tip assembly is coupled to the distal end of the lead body and includes a shell, a coupler, and a fixation helix. The shell has an outer wall defining a shell proximal end, an opposite shell distal end, and an internal cavity between the shell proximal and distal ends. The shell further includes a helix guide member extending across the cavity at or near the shell distal end and defining an axial surface and a distal opening. The coupler is rotatably disposed within the cavity and includes a proximal shaft portion mechanically coupled to the torque transmission member, and a distal shaft portion having a distal end. The coupler further includes a distal rotation stop member protruding axially from the distal end of the distal shaft portion, wherein rotation of the torque transmission member causes rotation of the coupler. The fixation helix is fixedly coupled to the distal shaft portion of the coupler and includes a distal portion extending at least partially through the distal opening of the shell. The fixation helix and the helix guide member are configured so that the fixation helix slidably contacts a portion of the helix guide member such that rotation of the torque transmission member, the coupler and the fixation helix causes axial translation of the coupler and the fixation helix relative to the shell between fully retracted and fully extended positions. The distal rotation stop member is configured to abut the axial surface of the helix guide member in the fully extended position so as to delimit further rotation and axial extension of the coupler and the fixation helix.

In Example 17, the implantable medical electrical lead of Example 16, wherein the cavity has a generally circular cross-sectional shape and the helix guide member has a generally semi-circular cross-sectional shape when viewed along the longitudinal axis of the lead, such that the distal opening has a generally semi-circular shape.

In Example 18, the medical electrical lead of either of Examples 16 or 17, wherein the distal end of the distal shaft portion of the coupler includes a distal radial face, and wherein the distal rotation stop member is disposed radially inward of the fixation helix and protrudes axially from the distal radial face.

In Example 19, the medical electrical lead of any of Examples 16-18, wherein the helix guide member extends radially inward of the outer wall of the shell.

In Example 20, the medical electrical lead of any of Examples 16-19 wherein the distal rotation stop member includes a pair of converging axial surfaces, and wherein one of the converging axial surfaces is configured to abut the axial surface of the helix guide member to delimit further rotation and extension of the coupler and the fixation helix.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
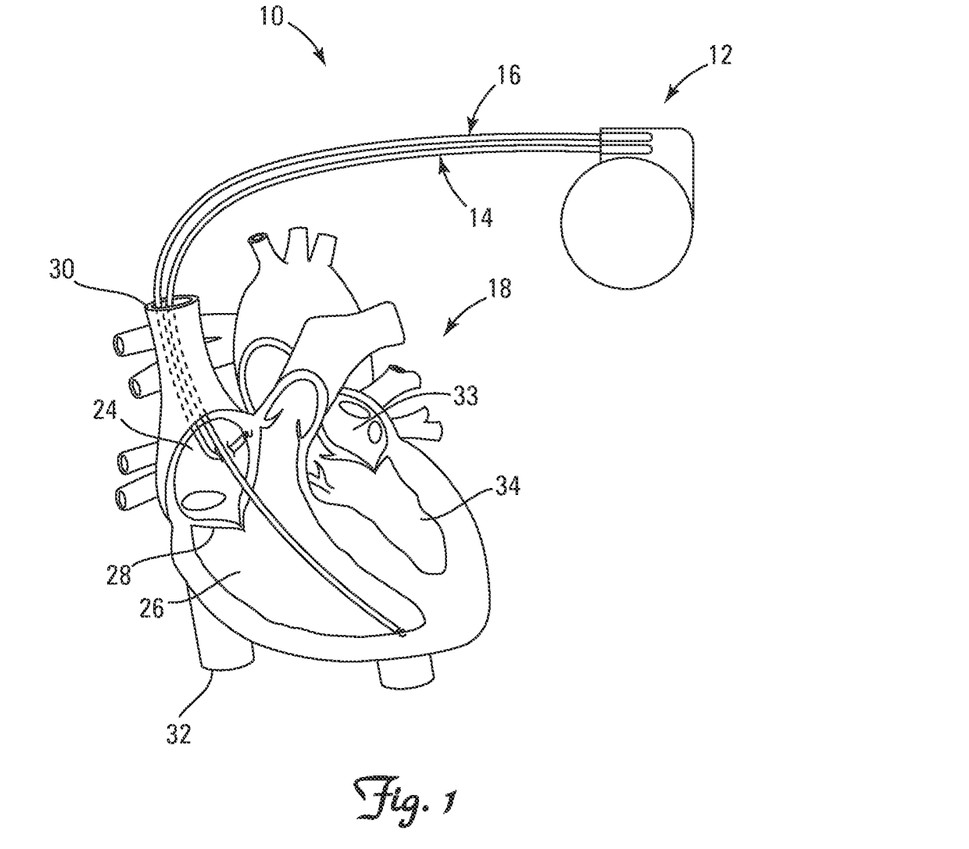
FIG. 1 is a schematic view of a cardiac rhythm management (CRM) system according to one embodiment.

FIG. 1 is a schematic view of a cardiac rhythm management (CRM) system 10 according to one embodiment. As shown in FIG. 1, the CRM system 10 includes a pulse generator 12 coupled to a plurality of leads 14, 16 deployed in a patient's heart 18. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. As further shown, the heart 18 includes a left atrium 33, which receives oxygenated blood from the lungs, and a left ventricle 34, which pumps the oxygenated blood to the body.

The leads 14, 16 operate to convey electrical signals and stimuli between the heart 18 and the pulse generator 12. In the illustrated embodiment, the lead 14 is implanted in the right ventricle 26, and the lead 16 is implanted in the right atrium 24. In other embodiments, the CRM system 10 may include additional leads, e.g., a lead extending into a coronary vein for stimulating the left ventricle in a bi-ventricular pacing or cardiac resynchronization therapy (CRT) system. As shown, the leads 14, 16 enter the superior vena cava 30, and are implanted in the right ventricle 26 and right atrium 24, respectively.

The pulse generator 12 is typically implanted subcutaneously within an implantation location or pocket in the patient's chest or abdomen. The pulse generator 12 may be any implantable medical device known in the art, or later developed, for delivering an electrical therapeutic stimulus to the patient. In various embodiments, the pulse generator 12 is a pacemaker, a CRT device, an implantable cardiac defibrillator, and/or includes both pacing, CRT and/or defibrillation capabilities (e.g., a CRT-D device).

As explained in greater detail herein, the leads 14, 16 are actively fixated to the cardiac tissue by a fixation helix that is configured to be screwed into the cardiac tissue. In the various embodiments, the fixation helix is a so-called "extendable/retractable" type in that it can be substantially or entirely retracted within the lead structure, e.g., during advancement of the lead 14 or 16 to the desired implantation site, and thereafter extended distally to expose a portion of the fixation helix so that it can be screwed into the endocardium. In some embodiments, the fixation helix is electrically active and thus can be used to sense the electrical activity of the heart 18 or to apply a stimulating pulse to the cardiac tissue. In other embodiments, the fixation helix is not electrically active and merely operates as a fixation means.

Figure 2A:
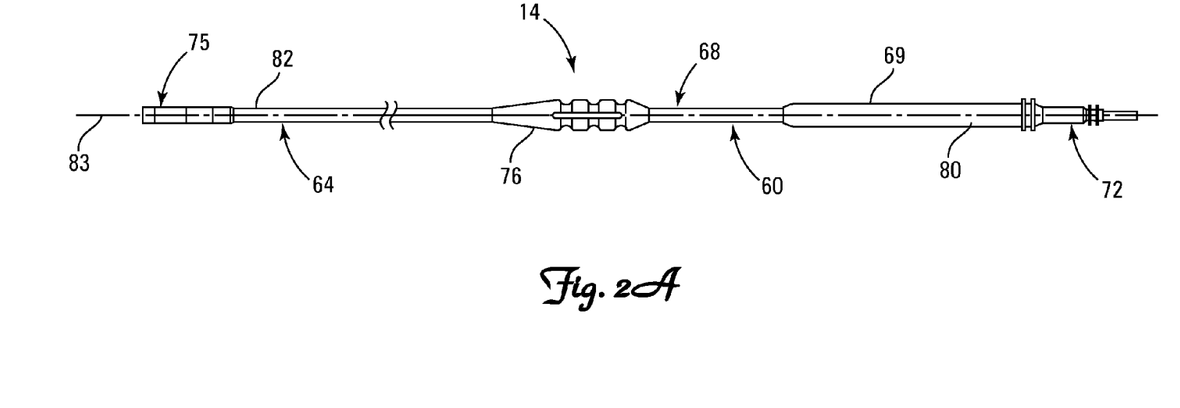
FIG. 2A is an elevation view of a lead of the CRM system of FIG. 1 in a non-implanted state.

FIG. 2A is an elevation view of the lead 14 in a non-implanted state. As shown in FIG. 2A, the lead 14 is defined by a proximal region 60 and a distal region 64. Generally speaking, the proximal region 60 is dimensioned so as to make up the portion of the lead 14 extending from the pulse generator 12 to the location at which the lead 14 enters the right atrium 24 via the superior vena cava 30, whereas the distal region 64 is dimensioned to extend within the heart 18 to the location at which the lead 14 is attached to the endocardium (see FIG. 1).

In the embodiment illustrated in FIG. 2A, the lead 14 includes a flexible body 68, a proximal connector 72, a distal tip assembly 75, and a suture sleeve 76. As shown, the body 68 includes a proximal end 80 and an opposite distal end 82. The proximal connector 72 is coupled to the proximal end 80 of the body 68, and the distal tip assembly 75 is coupled to the distal end 82 of the body 68. In the illustrated embodiment, the lead 14 includes a polymer boot 69 covering the proximal end 80 of the body 68 as well as a portion of the connector 72. Additionally, the elongate body 68 defines, in the illustrated embodiment, a longitudinal axis 83 of the lead 14. The boot 69 operates, when present, to reinforce the transition between the lead body 68 and the connector 72 as well as to provide a seal between the connector 72 and the header on the pulse generator 12 (see FIG. 1) to which the lead 14 is connected. The suture sleeve 76 provides a structure to support the lead 14 so that it can be sutured to fascia or muscular tissue to inhibit movement of the lead 14 after implantation. The operation of the boot 69 and the suture sleeve 76 is not critical to the various embodiments disclosed herein, and thus are not described in further detail.

Figure 2B:
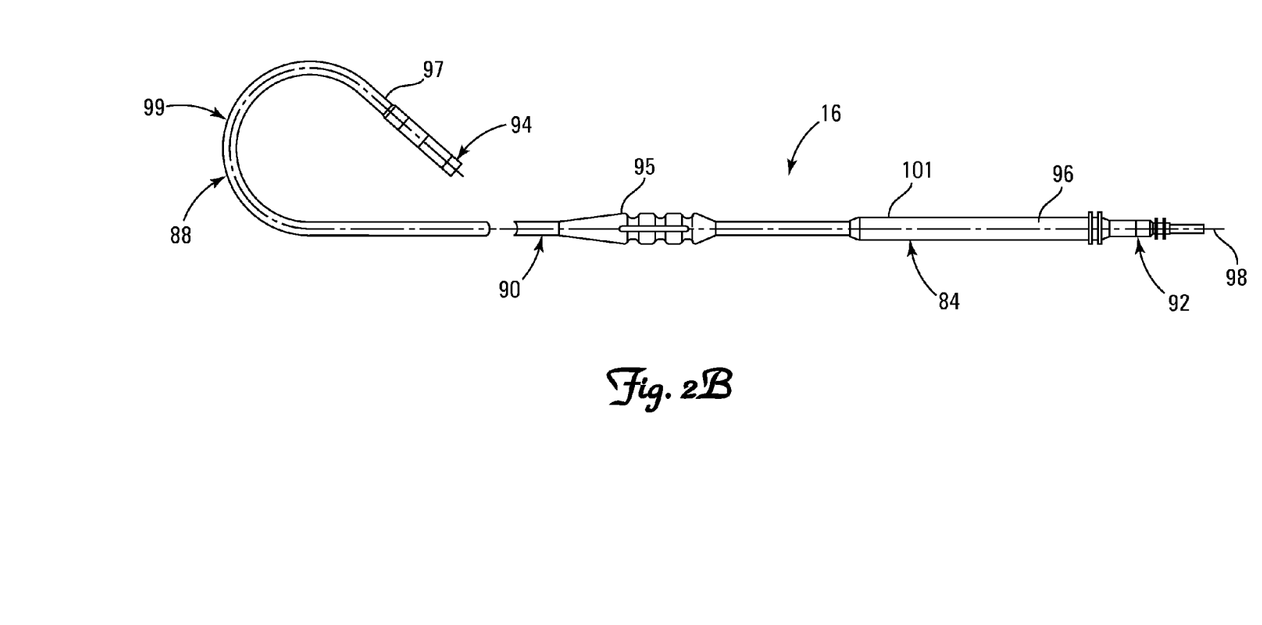
FIG. 2B is an elevation view of another lead of the CRM system of FIG. 1 in a non-implanted state.

FIG. 2B is an elevation view of the lead 16 in a non-implanted state. As can be seen in FIG. 2B, the lead 16 is in many respects similar or identical to the lead 14, and has a proximal region 84 and a distal region 88. Additionally, the lead 16 includes a flexible, elongate body 90, a proximal connector 92, a distal tip assembly 94 and a suture sleeve 95. As shown, the body 90 has a proximal end 96 and a distal end 97 opposite the proximal end 96. The proximal connector 92 is coupled to the proximal end 96 of the body 90, and the distal tip assembly 94 is coupled to the distal end 97 of the body 90, as in the lead 14. Similar to the lead 14, the lead body 90 defines a longitudinal axis 98 of the lead 16. Additionally, the lead 16 includes a polymer boot 101 covering the proximal end 96 of the body 90 as well as a portion of the connector 92. As can be seen in FIG. 2B, the lead 16 primarily differs structurally from the lead 14 in that the distal region 88 of the lead 16 includes a pre-formed curved portion 99 shaped into a J-shape to direct the tip assembly 94 toward the desired attachment location within the right atrium 24. The leads 14, 16 are otherwise generally identical, and so for expediency, various embodiments of the lead 14 will be described herein, although it is emphasized that the described features and functionality can be readily applied to a right atrial lead such as the lead 16.

Figure 3A:
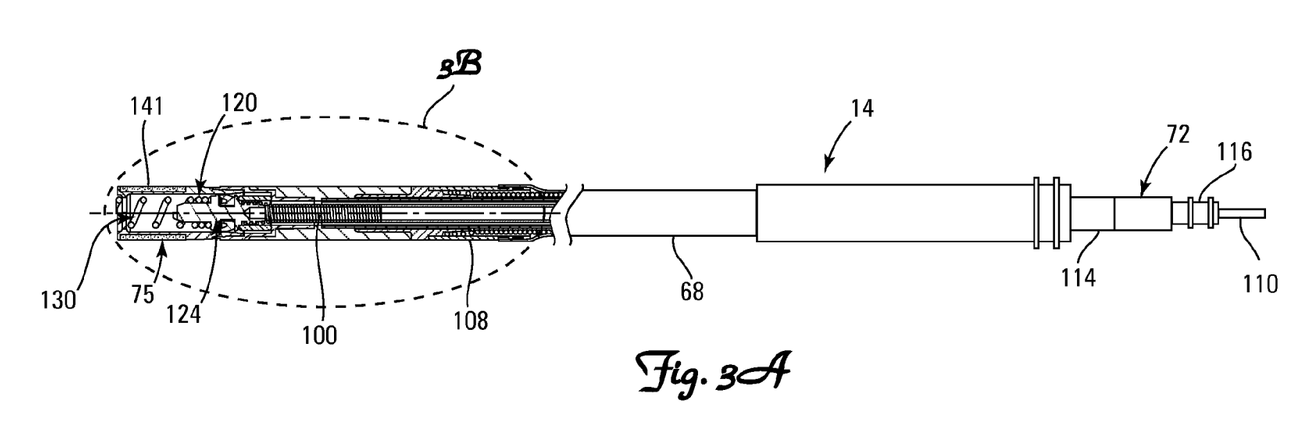
FIGS. 3A and 3B are partial cross-sectional views of the lead of FIG. 2A according to an exemplary embodiment.
Figure 3B:
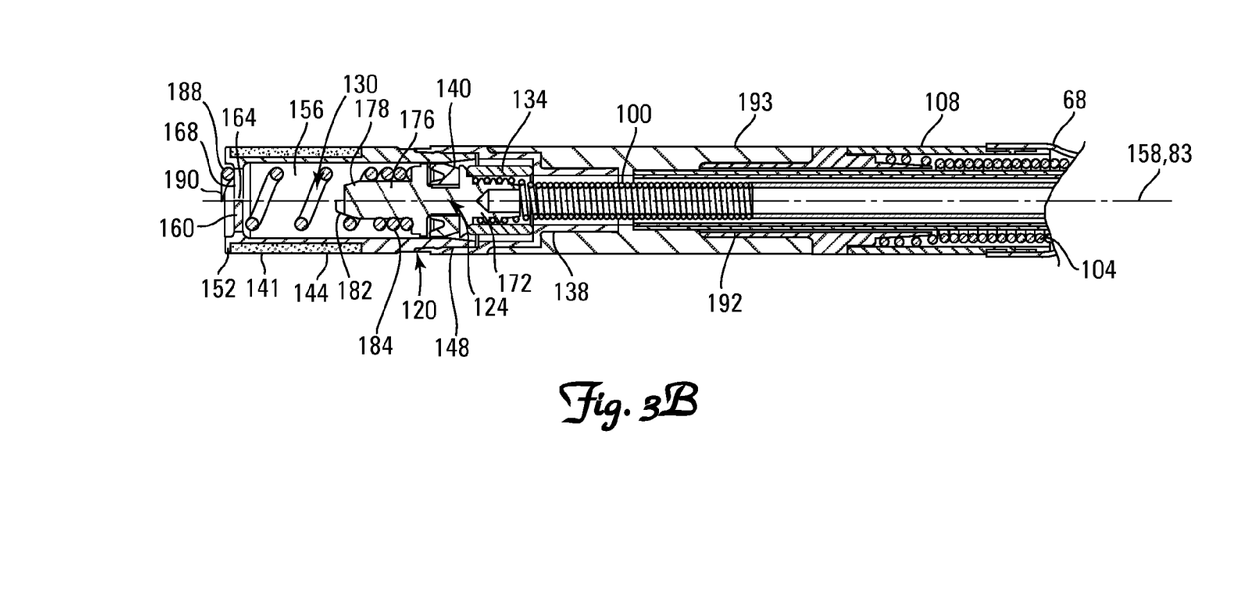

FIGS. 3A and 3B are partial cross-sectional views of the lead 14 according to an exemplary embodiment. As shown in FIGS. 3A and 3B, the lead 14 includes, in the illustrated exemplary embodiment, an inner coil conductor 100, an outer coil conductor 104, and a ring electrode assembly 108. Additionally, the connector 72 includes a terminal pin 110, a ring contact 114 and a seal member 116. In the illustrated embodiment, the connector 72 is a conventional bi-polar connector, e.g., an IS-1 connector, configured to mechanically and electrically couple the lead 14 to a header of the pulse generator 12 (see FIG. 1). As such, the ring contact 114 and the terminal pin 110 are each electrically conductive and electrically isolated from one another, and are adapted to engage a corresponding contact within the pulse generator header. In one embodiment, as discussed in further detail herein, the terminal pin 110 is rotatable relative to the ring contact 114 and the lead body 68, and is operable to facilitate extension and retraction of a fixation helix/electrode housed within the distal tip assembly 75. However, other embodiments may utilize other connector 72 configurations, depending on the configuration of the corresponding pulse generator 12.

As further shown, in the illustrated embodiment, the distal tip assembly 75 includes a shell 120, a coupler 124, a fixation helix 130, a weld sleeve 134, a rear plate 138, a seal member 140 and a drug collar 141. As illustrated, the shell 120 includes an outer wall 144 extending from a proximal end 148 to a distal end 152 and enclosing an internal cavity 156, and has a longitudinal axis 158 generally corresponding to the longitudinal axis 83 of the lead 14. Additionally, the shell 120 includes a helix guide member 160 extending across the cavity 156. The helix guide member 160 includes an axial surface 164 and defines a distal opening 168 into the cavity 156.

In the illustrated embodiment, the coupler 124 operates as a rotatable shaft, and thus is rotatably disposed within the cavity 156 and includes a proximal shaft portion 172 and a distal shaft portion 176 including a distal end 178. As further shown, the coupler 124 includes a distal rotation stop member 182 protruding axially from the distal end 178 of the coupler distal shaft portion 176.

In the embodiment of FIGS. 3A and 3B, the fixation helix 130 has a proximal portion 184 and a distal portion 188 terminating in a sharpened distal tip 190. As shown, the proximal portion 184 of the fixation helix 130 is coupled to the distal shaft portion 176 of the coupler 124. The fixation helix 130 can be fixedly attached to the distal shaft portion 176 by any mechanical attachment means or technique, e.g., welding, brazing, crimping, and the like. In one embodiment, as shown, the attachment strength of the fixation helix 130 to the distal shaft portion 176 is enhanced by virtue of threads formed onto the distal shaft portion 176, although this is not a requirement. In the illustrated embodiment, both the coupler 124 and the fixation helix 130 are made of an electrically conductive material.

The lead body 68 is in the form of a flexible, elongate tube of electrically insulative material, and the inner and outer coil conductors 100, 104 extend longitudinally within the lead body 68. In the illustrated embodiment, the coil conductors 100, 104 are configured in a coaxial, non-coradial configuration as is known in the art. Additionally, a tubular inner insulating sheath 192 is disposed between the inner and outer conductor coils 100, 104. However, in various embodiments, e.g., those in which the inner and outer coil conductors 100, 104 are separately insulated, the inner insulating sheath 192 may be omitted. In the illustrated embodiment, the lead body 68 is a multi-part structure and includes a distal segment 193 between the ring electrode assembly 108 and the distal tip assembly 75. However, in other embodiments, the lead body 69 may be a single, unitary tubular element. In short, the specific configuration of the lead body 68 is not of particular importance to the various embodiments, and so any number of lead body designs can be utilized.

In addition, although not visible in FIG. 3A or 3B, the inner and outer coil conductors 100, 104 are both mechanically and electrically connected to the terminal pin 110 and the ring contact 114, respectively, within the connector 72. Thus, because as explained elsewhere the terminal pin 110 is rotatable relative to the lead body 68, the inner conductor 100 is also rotatable within the lead body 68 and can operate as a torque transmission member to transmit torque applied to the terminal pin 110. In addition, the coiled configuration of the inner coil conductor 104 defines an inner lumen for receiving a stylet or similar instrument to facilitate delivery of the lead 14.

As illustrated, the outer coil conductor 104 is both mechanically and electrically connected to the ring electrode assembly 108, which operates as a low-voltage pace/sense electrode as is known. The specific design and construction of the ring electrode assembly 108 and/or the connection of the outer coil conductor 104 thereto are of no particular importance to the various embodiments. Thus any electrode or conductor design, whether now known or later developed, may be used in lieu of or in addition to the outer coil conductor 104 and/or the ring electrode assembly 108.

As also illustrated, the inner coil conductor 100 is fixedly coupled, both mechanically and electrically, to the proximal shaft portion 172 of the coupler. Thus, because both the coupler 124 and the fixation helix 130 are electrically conductive, the inner coil conductor 100 is configured to transmit electrical signals and/or stimuli between the terminal pin 110 and the fixation helix 130, which operates as a low voltage pace/sense electrode. Consequently, in the illustrated embodiment, the ring electrode assembly 108 and the fixation helix 130 combine to provide bi-polar pacing and sensing capabilities.

As previously explained, in the illustrated embodiment, the inner coil conductor 100 operates as a torque transmission member, such that rotation of the terminal pin 110 relative to the body 68 causes rotation of the coupler 124 and the fixation helix 130 relative to the shell 120. In turn, the fixation helix 130 is arranged within the shell 120 such that a surface of the fixation helix 130 contacts and slidably engages the helix guide member 160. This engagement of the fixation helix 130 and the helix guide member 160 thus causes the fixation helix 130 (and consequently, the coupler 124) to translate axially relative to the shell 120 as the fixation helix 130 rotates relative to the shell 120. Thus, in the various embodiments, the interaction of the fixation helix 130 and the helix guide member 160 effectuates the desired extension and retraction of the fixation helix 130 as the terminal pin 110 is rotated by the implanting physician. In this respect, the fixation helix 130 and helix guide member 160 operate in substantially the same manner as the fixation helix and the guide elements disclosed in co-pending and commonly assigned U.S. application Ser. No. 12/785,941, the contents of which are incorporated herein by reference.

In various embodiments, the seal member 140 operates to substantially prevent ingress of bodily fluids into the internal region of the lead 14, and in the illustrated embodiment is capable of translating axially within the shell 120 along with the coupler 124. In one embodiment, the seal member 140 can be configured to be substantially the same as or identical to any of the shaft seals disclosed in co-pending and commonly assigned U.S. application Ser. No. 12/818,691, the contents of which are incorporated herein by reference. In other embodiments, however, other seal configurations are employed, or alternatively, a shaft seal can be omitted altogether. Additionally, the drug collar 141 can be any drug eluting element such as are known in the art.

As shown, the distal rotation stop member 182 is positioned radially inward of the fixation helix 130. In various embodiments, the distal rotation stop 182 is sized and shaped so as to abut the axial surface 164 of the helix guide member 160 upon a pre-determined amount of extension of the coupler 124 relative to the shell 120. That is, the coupler 124 and the fixation helix 130 can be advanced distally (again, by rotation of the terminal pin 110 relative to the lead body 68) until the distal rotation stop 182 abuts the axial surface 164, at which point further rotation of the coupler 124 in the extension direction is prevented. Accordingly, the interaction of the distal rotation stop 182 and the axial surface 164 operates to delimit rotation, and consequently, axial extension of the coupler 124 and the fixation helix 130 beyond a predetermined limit. This will advantageously prevent over-rotation of the coupler 124 and the fixation helix 130, and thus will tend to maintain desired radial alignment of the fixation helix 130 relative to the shell 120. If this radial alignment is not maintained, the potential could exist for the fixation helix 130 to wedge against the helix guide member 160. The operation of the distal rotation stop 182 and the axial surface 164 thus promotes smooth operation of the fixation helix 130, in particular, smooth retraction of the fixation helix 130 after it has been fully extended.

In addition, in various embodiments, the weld sleeve 134 and the rear plate 138 may include mating teeth or similar projections that interact to delimit further rotation of the coupler 124 once the coupler 124 and the fixation helix 130 are fully retracted within the shell 120.

In various embodiments, it may be desirable to maintain part of the distal portion 188 of the fixation helix 130 extending distally beyond the helix guide member 160 even when the fixation helix 130 is fully retracted. This ensures that the fixation helix 130 will engage the helix guide member 160 to allow for extension of the fixation helix 130, and also advantageously enables the physician to use the electrically active fixation helix 130 to map cardiac tissue and thereby identify an optimal attachment site. In the illustrated embodiment, helix guide member 160 is recessed a nominal amount from the distal end 152 of the shell 124. Recessing the helix guide member 160 in this manner allows the distal tip 190 of the fixation helix 130 to extend distally beyond the helix guide member 160 for the aforementioned reasons, while at the same time utilizes the portion of the shell 120 extending beyond the helix guide member 160 to at least partially shield the exposed portion of the fixation helix 130 from body tissue. This configuration advantageously inhibits unintended interaction between the fixation helix 130 and the vascular or cardiac tissue, e.g., during delivery and deployment of the lead 14.

Figure 4:
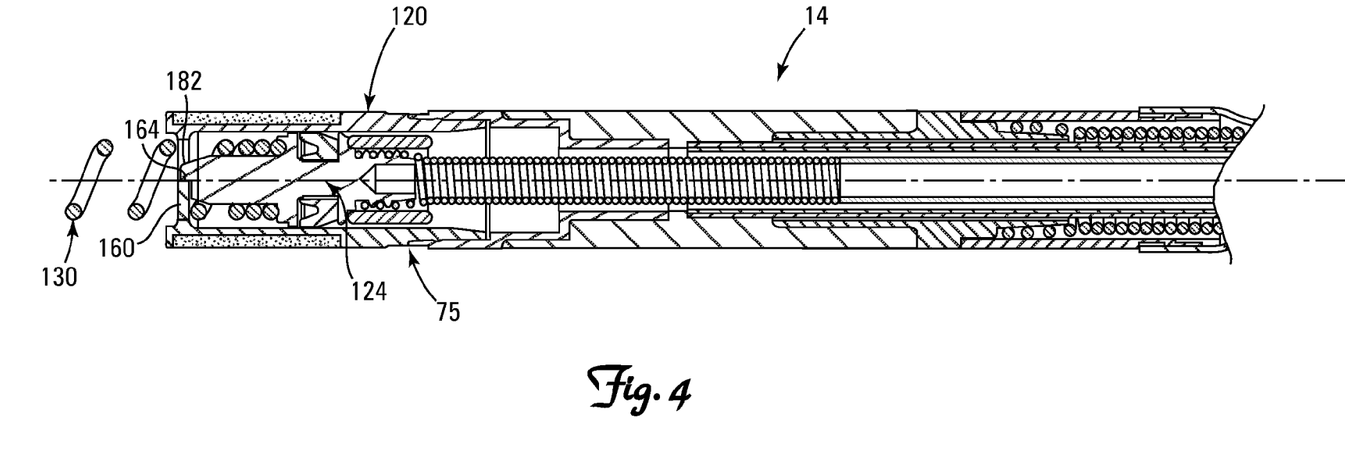
FIG. 4 is a partial cross-sectional view of the portion of the lead of FIG. 2A shown in FIG. 3B but with its fixation helix in its fully extended state.

FIG. 4 is a partial cross-sectional view of the portion of the lead 14 shown in FIG. 3 but with the fixation helix 130 in its fully extended state. As shown in FIG. 4, the coupler 124 of the distal tip assembly 75 is advanced distally within the shell 120 (as compared to its substantially fully retracted state shown in FIGS. 3A&B). In this position, the distal rotation stop 182 abuts the axial surface 164 of the helix guide member 160 so as to prevent further rotation and axial extension of the coupler 124. At the same time, however, the engagement of the distal rotation stop 182 and the axial surface 164 provides little to no resistance to reverse rotation and retraction of the coupler 124.

Figure 5A:
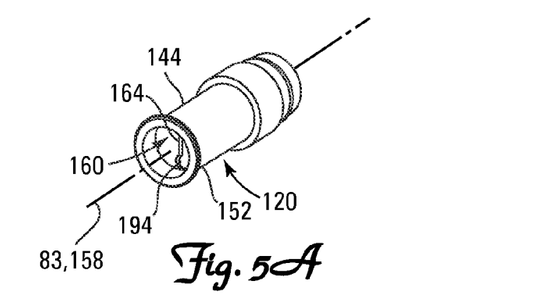
FIGS. 5A-5B are perspective and distal end elevation views of a distal tip assembly shell for use in the lead of FIG. 2A according to one embodiment.
Figure 5B:
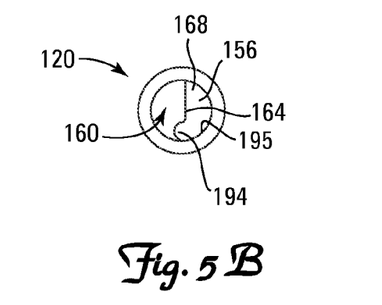

FIGS. 5A-5B are perspective and distal end elevation views of the shell 120 according to one embodiment. As shown in FIGS. 5A-5B, the shell 120 and the cavity 156 have a generally circular cross-sectional shape, and the helix guide member 160 has a generally semi-circular shape, e.g., a D-shape. In the illustrated embodiment, the axial surface 164 of the helix guide member 160 includes a radiused region 194 near the intersection of the axial surface 164 and an inner surface 195 of the shell outer wall 144. The radiused region 194 can generally facilitate ease of manufacturing of the shell 120 by accommodating tooling used to form the shell 120. Of course, in other embodiments, the radiused region 194 can be omitted.

In general, the configuration of the helix guide member 160 determines the size and shape of the distal opening 168 at or near the distal end 152 of the shell 120. Accordingly, in the illustrated embodiment, the distal opening 168 also has a generally semi-circular shape. The presence of the distal opening 168 can, in various embodiments, allow ingress of blood and tissue into the cavity 156, which can improve the strength of the attachment of the lead 14 to the heart 18. In various embodiments, the size and shape of the helix guide member 160 can be tailored to provide optimal performance of the distal tip assembly 75, and at the same time provide a desired amount of tissue ingrowth into the cavity 156.

In the illustrated embodiment, the helix guide member 160 is sized and positioned so that the axial surface 164 extends through the longitudinal axis 158 of the shell 120, and consequently, also extends through the longitudinal axis 83 of the lead 14 (see FIG. 3B). Thus, the helix guide member 160 and the distal opening 168 have the same general size and shape, and will substantially mirror each other (when viewed along the longitudinal axes 83, 158). In other embodiments, the helix guide member 160 has a semi-circular D-shape similar to the embodiment shown in FIGS. 5A-5B, but the axial surface 164 is radially offset from the longitudinal axis 158 of the shell 120 and the longitudinal axis 83 of the lead 14. Consequently, in such embodiments, the distal opening 168 has a larger cross-sectional area than the helix guide member 160 when viewed along the axes 83, 158.

Figure 6A:
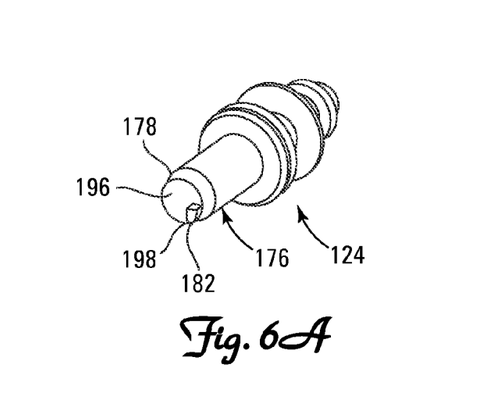
FIGS. 6A-6B are perspective and distal end elevation views of a distal tip assembly coupler for use in the lead of FIG. 2A according to one embodiment.
Figure 6B:
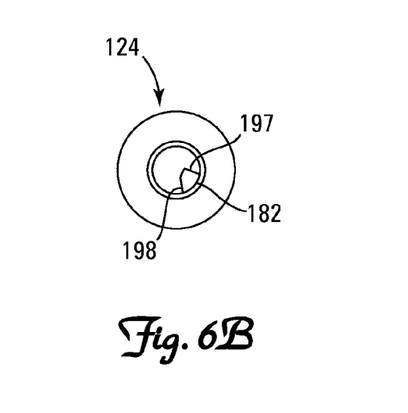

FIGS. 6A-6B are perspective and distal end elevation views of the coupler 124 according to one embodiment. As shown in FIGS. 6A-6B, the coupler 124 has a distal radial face 196 at the distal end 178 of the distal shaft portion 176, and the distal rotation stop member 182 protrudes axially from this distal radial face 196. As further shown, the distal rotation stop member 182 generally has a shape of a partial pie piece with its "tip" omitted. As such, the distal rotation stop member 182 includes a pair of converging axial surfaces 197, 198, with the axial surface 197 configured to abut the axial surface 164 of the helix guide member 160 to delimit rotation and extension of the coupler 124 and the fixation helix 130 as described elsewhere. The shape of the distal rotation stop member 182 illustrated in FIGS. 6A-6B, i.e. can promote smooth operation of the distal tip assembly 75 (FIG. 2A) by promoting pure rotational movement of the coupler 124 in the retraction direction. That is, omission of the "tip" of the pie piece-shaped distal rotation stop member 182 can eliminate the likelihood that the distal rotation stop member 182 will pivot about the point of the "tip" (if present). Such pivoting movement would tend to urge the coupler 124 radially thereby tending to resist rotation of the coupler 124.

In various other embodiments, the distal rotation stop 182 can take on other cross-sectional shapes. For example, in one embodiment, the distal rotation stop member 182 has a pie piece shape. In one embodiment, the distal rotation stop member 182 has a generally circular cross-sectional shape. In still other embodiments, the distal rotation stop member 182 can have other cross-sectional shapes, e.g., rectangular, elliptical, etc.

The various components of the lead 14 can be made from any known or later developed lead construction materials. For example, the lead body 68 can be made from any flexible, electrically insulative material suitable for human implantation. Exemplary materials for use as the body 68 can include polyurethane, silicone rubber, and co-polymers of both, and can include surface or other treatments (e.g., plasma treatments, lubricious coatings, and the like) based on the functional requirements of the lead 14. The coil conductors 100, 104 can also be made of any known or later developed lead conductor materials.

Similarly, the components of the distal tip assembly 75 can be any known or later developed materials. In various embodiments, the shell 120 is made of a non-electrically conductive material such as polyether sulfone (PES), polyurethane-based thermoplastics, ceramics, polypropylene and polyetheretherketone (sold under the brand name PEEK™). Additionally, the coupler 124 and the fixation helix 130 can be made of any known or later developed conductive material, typically a metal such as Elgiloy, MP35N, tungsten, tantalum, iridium, platinum, titanium, palladium, stainless steel as well as alloys of any of these materials. In various embodiments, the fixation helix 130 can include a surface treatment or coating, such as a coating of iridium oxide, to enhance the electrical performance of the helix 130. Alternatively, the coupler 124 and/or the fixation helix 130 can be made of non-electrically conductive materials such as any of the materials described previously with respect to the shell 120. Similarly, in various embodiments utilizing a conductive shell 120, the shell can be made of any of the materials described with respect to the coupler 124 and the fixation helix 130.

Figure 7A:
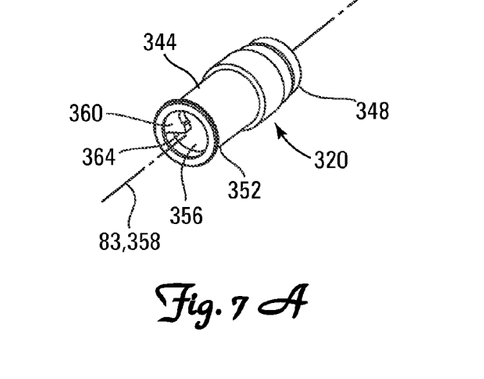
FIGS. 7A-7B are perspective and distal end elevation views of an alternative distal tip assembly shell for use in the lead of FIG. 2A according to another embodiment.
Figure 7B:
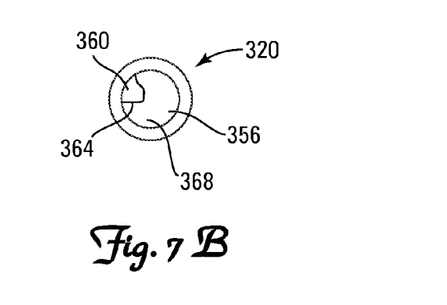

In various embodiments, the helix guide member 160 can have a shape other than the semi-circular D-shape of the embodiment of FIGS. 5A-5B. For example, FIGS. 7A-7B are perspective and distal end elevation views of an alternative shell 320 for use in a lead distal tip assembly according to another embodiment. As shown in FIGS. 7A-7B, the shell 320 is in most respects similar or identical to the shell 120, and includes an outer wall 344 extending from a proximal end 348 to a distal end 352 and enclosing an internal cavity 356, and has a longitudinal axis 358 generally corresponding to the longitudinal axis 83 of the lead 14 (see FIG. 2A). Additionally, the shell 320 includes a helix guide member 360 in the form of a radial projection extending radially inward of the outer wall 344 of the shell 320. In this embodiment, the helix guide member 360 thus has an axial surface 364 dimensioned and positioned so that it will be engaged by the distal rotation stop member 182 of the coupler 124 as described herein to delimit further rotation and extension of the coupler 124 and the fixation helix 130 (see FIGS. 3B & 4). In the illustrated embodiment, the helix guide member 360 does not extend radially inward to the longitudinal axis 358 or the longitudinal axis 83 of the lead 14. In various other embodiments, the helix guide member 360 can extend to or beyond the longitudinal axes 83, 358. The configuration of the helix guide member 360 thus provides for a relatively large distal opening 368 (as compared to other embodiments described herein).

Figure 8A:
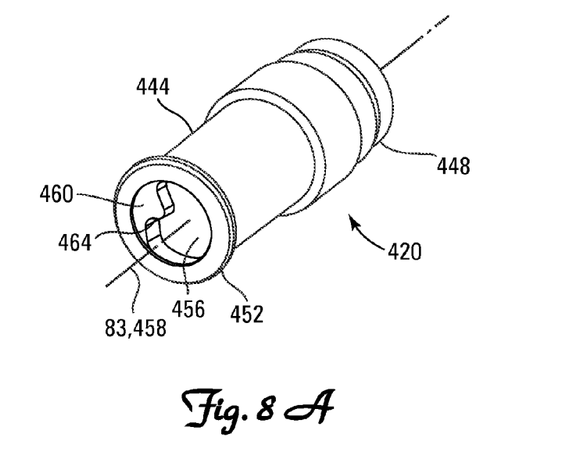
FIGS. 8A-8B are perspective and distal end elevation views of another alternative distal tip assembly shell for use in the lead of FIG. 2A according to yet another embodiment.
Figure 8B:
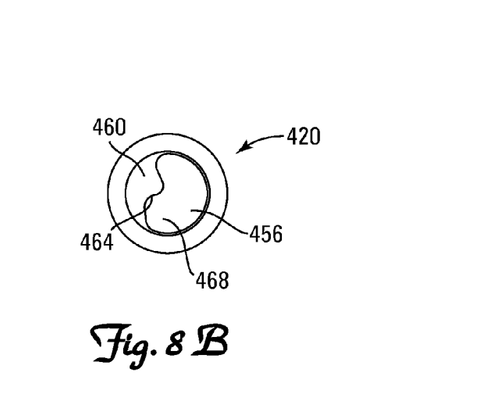

FIGS. 8A-8B are perspective and distal end elevation views of another alternative shell 420 for use in a lead distal tip assembly according to yet another embodiment. As shown in FIGS. 8A-8B, the shell 420 is in most respects similar or identical to shells 120 and 320 (FIGS. 5A and 7A, respectively), and includes an outer wall 444 extending from a proximal end 448 to a distal end 452 and enclosing an internal cavity 456, and has a longitudinal axis 458 generally corresponding to the longitudinal axis 83 of the lead 14 (see FIG. 2A). Additionally, the shell 420 includes a helix guide member 460 in the form of a radial projection extending radially inward of the outer wall 444 of the shell 320 along with portions that extend along the outer wall 444. In this embodiment, the helix guide member 460 thus has an axial surface 464 dimensioned and positioned so that it will be engaged by the distal rotation stop member 182 of the coupler 124 as described herein to delimit further rotation and extension of the coupler 124 and the fixation helix 130 (see FIGS. 3B & 4). In the illustrated embodiment, the helix guide member 460 does not extend radially inward to the longitudinal axis 458 or the longitudinal axis 83 of the lead 14. In various other embodiments, the helix guide member 460 can extend to or beyond the longitudinal axes 83, 458. The configuration of the helix guide member 460 thus provides for a relatively large distal opening 468 (as compared to some other embodiments described herein), similar to the opening 368 in FIGS. 7A-7B. The shape and size of helix guide member 460 is yet another example of such a feature that may be included in the claimed implantable medical electrical lead. However, other sizes and shapes are also contemplated.

While the embodiments described herein have been primarily in connection with the lead 14, it is emphasized that the distal tip assembly 75 is also advantageously utilized in the J-shaped atrial lead 16. In various embodiments, the J-shape of the lead 16 results in relatively high torque requirements to rotate the fixation helix 130 due to the need for the torque transmission element (i.e., the inner coil conductor 100) to traverse and rotate through the J-shaped region of the lead 16. Such torque requirements would otherwise create the potential for over extension and wedging of the fixation helix of the lead 16 against the helix guide member, which is substantially prevented by the inclusion of the distal rotation stop member and the interaction of the distal rotation stop member with the axial surface of the helix guide member as described with respect to the lead 14.

Additionally, while the lead 14 has been described herein as having an electrically active fixation helix 130 operating as a pace/sense tip electrode, in other embodiments, the fixation helix 130 can be electrically inactive and thus operate solely as a fixation element. In such embodiments, for example, the lead 14 may be a unipolar lead. In other embodiments, the lead 14 may include a second ring electrode in addition to the ring electrode assembly 108. For example, in one embodiment, the shell 120 (or the shell 220, 320 or 420) can be made from an electrically conductive material and can be electrically and mechanically coupled to the inner coil conductor 100 or a different coil or cable conductor. Any number of different conductor and/or electrode configurations are contemplated within the scope of the disclosed embodiments.

Furthermore, while the lead 14 utilizes the terminal pin 110 and the inner coil conductor 100 as torque transmission means, in other embodiments, a stylet or similar instrument may be used to rotate the coupler 124 to actuate the fixation helix 130. In still another embodiment, the coupler 124 may be coupled to a torque transmission member (e.g., a metallic or polymeric coil) extending within the lead body 68 and coupled to the rotatable terminal pin 110 but which may be electrically non-conductive. In such embodiments, the terminal pin 110 may still be utilized to rotate and extend/retract the fixation helix 130, but the fixation helix 130 need not be electrically active.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable medical electrical lead comprising:
   a flexible insulative body having a proximal end and an opposite distal end, the body defining a longitudinal axis of the lead;
   a connector coupled to the proximal end of the lead body configured for operatively coupling the lead to an implantable pulse generator;
   a first conductor extending within the lead body from the connector toward the distal end of the lead body;
   a first electrode coupled to the body and to the first conductor; and
   a distal tip assembly coupled to the distal end of the lead body including:
      a shell having an outer wall defining a shell proximal end, an opposite shell distal end, and an internal cavity between the shell proximal and distal ends, the shell further including a helix guide member extending at least partially across the cavity at or near the shell distal end and defining an axial surface and a distal opening bounded by an inner wall defined by the helix guide member and the outer wall of the shell;
      a coupler rotatably disposed within the cavity including a proximal shaft portion and a distal shaft portion having a distal end, the coupler further including a distal rotation stop member protruding axially from the distal end of the distal shaft portion, the distal rotation stop member defining an axial surface parallel with the longitudinal axis of the lead and being sized to be received within the distal opening so that a portion of the coupler extends beyond the inner wall;
a fixation helix fixedly coupled to the distal shaft portion of the coupler and including a distal portion extending at least partially through the distal opening of the shell,
wherein the fixation helix and the helix guide member are configured so that the fixation helix slidably contacts a portion of the helix guide member so that rotation of the coupler and the fixation helix causes axial translation of the coupler and the fixation helix relative to the shell between fully retracted and fully extended positions, and
wherein the distal rotation stop member is configured to abut the axial surface of the helix guide member in the fully extended position so as to delimit further rotation and axial extension of the coupler and the fixation helix.

2. The implantable medical electrical lead of claim 1, further comprising a second conductor extending within the lead body and connected to the proximal shaft portion of the coupler, and wherein the coupler and the fixation helix are electrically conductive and the fixation helix is operable as a second electrode.

3. The implantable medical electrical lead of claim 1, wherein the cavity has a generally circular cross-sectional shape and the helix guide member has a generally semi-circular cross-sectional shape when viewed along the longitudinal axis of the lead, such that the distal opening has a generally semi-circular shape.

4. The medical electrical lead of claim 3, wherein the axial surface of the helix guide member includes a radiused region near an intersection of the axial surface of the helix guide member and an inner surface of the shell outer wall.

5. The medical electrical lead of claim 1, wherein the distal end of the distal shaft portion of the coupler includes a distal radial face, and wherein the distal rotation stop member is disposed radially inward of the fixation helix and protrudes axially from the distal radial face.

6. The medical electrical lead of claim 1, wherein the helix guide member extends radially inward of the outer wall of the shell.

7. The medical electrical lead of claim 6, wherein the helix guide member does not extend radially inward to the longitudinal axis.

8. The medical electrical lead of claim 1, wherein the distal rotation stop member includes a pair of converging axial surfaces, and wherein one of the converging axial surfaces is configured to abut the axial surface of the helix guide member to delimit further rotation and extension of the coupler and the fixation helix.

9. An implantable medical electrical lead comprising:
a flexible insulative body having a proximal end and an opposite distal end, the body defining a longitudinal axis of the lead;
a connector coupled to the proximal end of the lead body configured for operatively coupling the lead to an implantable pulse generator, the connector including a rotatable terminal pin;
a first conductor extending within the lead body from the connector toward the distal end of the lead body, the first conductor fixedly coupled to the terminal pin and rotatable within the lead body; and
a distal tip assembly coupled to the distal end of the lead body including:
a shell having an outer wall defining a shell proximal end, an opposite shell distal end, and an internal cavity between the shell proximal and distal ends, the shell further including a helix guide member extending across the cavity at or near the shell distal end and defining an axial surface and a distal opening bounded by an inner wall defined by the helix guide member and the outer wall of the shell;
a coupler rotatably disposed within the cavity including a proximal shaft portion connected to the first conductor such that rotation of the terminal pin causes rotation of the coupler, and a distal shaft portion having a distal end, the coupler further including a distal rotation stop member protruding axially from the distal end of the distal shaft portion;
a fixation helix fixedly coupled to the distal shaft portion of the coupler and including a distal portion extending at least partially through the distal opening of the shell, the distal rotation stop member defining an axial surface parallel with the longitudinal axis of the lead and being sized to be received within the distal opening so that a portion of the coupler extends beyond the inner wall,
wherein the fixation helix and the helix guide member are configured so that the fixation helix slidably contacts a portion of the helix guide member so that rotation of coupler and the fixation helix causes axial translation of the coupler and the fixation helix relative to the shell between fully retracted and fully extended positions, and
wherein the distal rotation stop member is configured to abut the axial surface of the helix guide member in the fully extended position so as to delimit further rotation and axial extension of the coupler and the fixation helix.

10. The implantable medical electrical lead of claim 9, wherein the cavity has a generally circular cross-sectional shape and the helix guide member has a generally semi-circular cross-sectional shape when viewed along the longitudinal axis of the lead, such that the distal opening has a generally semi-circular shape.

11. The medical electrical lead of claim 10, wherein the axial surface of the helix guide member includes a radiused region near an intersection of the axial surface of the helix guide member and an inner surface of the shell outer wall.

12. The medical electrical lead of claim 9, wherein the distal end of the distal shaft portion of the coupler includes a distal radial face, and wherein the distal rotation stop member is disposed radially inward of the fixation helix and protrudes axially from the distal radial face.

13. The medical electrical lead of claim 9, wherein the helix guide member extends radially inward of the outer wall of the shell.

14. The medical electrical lead of claim 13, wherein the helix guide member does not extend radially inward to the longitudinal axis.

15. The medical electrical lead of claim 9, wherein the distal rotation stop member includes a pair of converging axial surfaces, and wherein one of the converging axial surfaces is configured to abut the axial surface of the helix guide member to delimit further rotation and extension of the coupler and the fixation helix.

* * * * *